(12) United States Patent
Parthun et al.

(10) Patent No.: US 11,369,549 B2
(45) Date of Patent: Jun. 28, 2022

(54) ANTISEPTIC WIPES

(71) Applicant: Medline Industries, LP, Northfield, IL (US)

(72) Inventors: William Parthun, Lake Forest, IL (US); Martin Coffey, Buffalo Grove, IL (US); Alannah Minarcik, Palatine, IL (US)

(73) Assignee: Medline Industries, LP, Northfield, IL (US)

( * ) Notice: Subject to any disclaimer, the term of this patent is extended or adjusted under 35 U.S.C. 154(b) by 236 days.

(21) Appl. No.: 16/157,263

(22) Filed: Oct. 11, 2018

(65) Prior Publication Data

US 2019/0110962 A1   Apr. 18, 2019

Related U.S. Application Data

(60) Provisional application No. 62/571,627, filed on Oct. 12, 2017.

(51) Int. Cl.
| | | |
|---|---|---|
| *A61K 8/02* | (2006.01) |
| *A61K 8/34* | (2006.01) |
| *A61K 8/41* | (2006.01) |
| *A61K 8/43* | (2006.01) |
| *A61K 8/891* | (2006.01) |
| *A61Q 17/00* | (2006.01) |
| *A61Q 19/10* | (2006.01) |

(52) U.S. Cl.
CPC .............. *A61K 8/0208* (2013.01); *A61K 8/34* (2013.01); *A61K 8/416* (2013.01); *A61K 8/43* (2013.01); *A61K 8/891* (2013.01); *A61Q 17/005* (2013.01); *A61Q 19/10* (2013.01)

(58) Field of Classification Search
None
See application file for complete search history.

(56) References Cited

U.S. PATENT DOCUMENTS

| | | |
|---|---|---|
| 3,855,140 A | 12/1974 | Billany |
| 3,960,745 A | 6/1976 | Billany |
| 4,420,484 A | 12/1983 | Gorman |
| RE32,300 E | 12/1986 | Gorman |

(Continued)

FOREIGN PATENT DOCUMENTS

| | | |
|---|---|---|
| GB | 2518607 | 4/2015 |
| KR | 102017003745 A | 1/2017 |

OTHER PUBLICATIONS

Gibbons et al., "Selecting and Ordering Populations: A new Statistical Methodology", Mathematics, 1999, pp. 1-594 (1 page is attached) (Year: 1999).*

(Continued)

*Primary Examiner* — Kyung S Chang
(74) *Attorney, Agent, or Firm* — Fitch, Even, Tabin & Flannery LLP

(57) ABSTRACT

A wipe includes a cleansing composition disposed on a cloth. The cleansing composition can include an antiseptic, a humectant, an emollient, a surfactant, and a monohydric alcohol. A wipe can be made by preparing a cleansing composition and disposing the cleansing composition on a cloth. Two or more wipes may be included in a sealed package to maintain the sterile state of the wipes. A method of disinfecting skin can include applying a wipe to skin.

20 Claims, 1 Drawing Sheet

(56) References Cited

U.S. PATENT DOCUMENTS

| | | | |
|---|---|---|---|
| 5,019,096 | A | 5/1991 | Fox, Jr. |
| 5,164,107 | A | 11/1992 | Khan |
| 5,334,388 | A | 8/1994 | Hoang |
| 5,335,373 | A | 8/1994 | Dresdner |
| 5,357,636 | A | 10/1994 | Dresdner |
| 5,487,896 | A | 1/1996 | Modak |
| 5,538,353 | A | 7/1996 | DeHavilland |
| 5,665,742 | A | 9/1997 | Mori |
| D386,849 | S | 11/1997 | DeHavilland |
| 5,690,958 | A | 11/1997 | McGrath |
| 5,705,532 | A | 1/1998 | Modak |
| 5,752,363 | A | 5/1998 | Edwards |
| 5,763,412 | A | 6/1998 | Khan |
| 5,772,346 | A | 6/1998 | Edwards |
| D396,911 | S | 8/1998 | DeHavilland |
| 5,956,794 | A | 9/1999 | Skiba |
| 5,965,610 | A | 10/1999 | Modak |
| 6,029,809 | A | 2/2000 | Skiba |
| 6,037,386 | A | 3/2000 | Modak |
| 6,066,674 | A | 5/2000 | Hioki |
| 6,458,341 | B1 | 10/2002 | Rozzi |
| D468,424 | S | 1/2003 | Stephane |
| 6,536,975 | B1 | 3/2003 | Tufts |
| 6,605,666 | B1 | 8/2003 | Scholz |
| 6,723,689 | B1 | 4/2004 | Hoang |
| 6,729,786 | B1 | 5/2004 | Tufts |
| 6,733,745 | B2 | 5/2004 | Rozzi |
| 6,991,393 | B2 | 1/2006 | Tufts |
| 6,991,394 | B2 | 1/2006 | Tufts |
| 7,030,203 | B2 | 4/2006 | Mosbey |
| 7,066,916 | B2 | 6/2006 | Keaty |
| 7,182,536 | B2 | 2/2007 | Tufts |
| 7,241,065 | B2 | 7/2007 | Tufts |
| 7,427,574 | B2 | 9/2008 | Allen |
| 7,595,021 | B2 | 9/2009 | Keaty, Jr. |
| 7,717,889 | B2 | 5/2010 | Keaty, Jr. |
| 7,935,093 | B2 | 5/2011 | Hanifl |
| 8,173,147 | B2 | 5/2012 | Creevy |
| 8,221,365 | B2 | 7/2012 | Keaty, Jr. |
| 10,124,067 | B2 | 11/2018 | Balbinot |
| 2002/0022660 | A1 | 2/2002 | Jampani |
| 2002/0086039 | A1* | 7/2002 | Lee .......................... C03C 3/097 424/401 |
| 2002/0187181 | A1 | 12/2002 | Godbey |
| 2003/0138492 | A1 | 7/2003 | Rozzi |
| 2003/0149106 | A1 | 8/2003 | Mosbey |
| 2004/0247655 | A1 | 12/2004 | Asmus |
| 2007/0138439 | A1 | 6/2007 | Asmus |
| 2007/0202177 | A1 | 8/2007 | Hoang |
| 2007/0231051 | A1 | 10/2007 | Flores |
| 2007/0248399 | A1 | 10/2007 | Tufts |
| 2008/0145390 | A1 | 6/2008 | Taylor |
| 2008/0199535 | A1 | 8/2008 | Taylor |
| 2009/0104281 | A1 | 4/2009 | Taylor |
| 2013/0344122 | A1 | 12/2013 | Isaac |
| 2014/0135297 | A1 | 5/2014 | Narayanan |
| 2016/0021888 | A1 | 1/2016 | Burke |
| 2017/0188578 | A1 | 7/2017 | Gundlapalli |

OTHER PUBLICATIONS

International Search Report and Written Opinion from PCT/US2018/055373, dated May 3, 2019; 11 pages.

"Prevalence of ceftriaxone- and ceftazidime-resistant gram-negative bacteria in longterm-care facilities," Infection Control and Hospital Epidemiology, vol. 22, No. 4 (Apr. 2001) pp. 193-197.

Akamatsu et al., "Transmission of helicobacter pylori infection via flexible fiberoptic endoscopy," American Journal of Infection Control (1996) pp. 396-401.

Ayliffe et al., "A comparison of pre-operative bathing with chlorhexidine-detergent and non-medicated soap in the prevention of wound infection," Journal of Hospital Infection (1983) pp. 237-244.

Bailey et al., "Virucidal activity of chlorhexidine on strains of herpesvirus hominis, poliovirus, and adenovirus," J. clin. Path., (Jun. 4, 2002) pp. 76-78.

Bartzokas et al., "A comparison of triclosan and chlorhexide preparations with 60 per cent isopropyl alcohol for hygienic hand disinfection," Journal of Hospital Infection (1983) 4, pp. 245-255.

Beeuwkes, et al., "Microbiological tests on operating-theatre staff of a new disinfectant foam based on 1% chlorhexidine gluconate," Journal of Hospital Infection (1986) pp. 200-202.

Butz et al., "Alcohol-impregnated wipes as an alternative in hand hygiene," American Journal of Infection Control (1990) pp. 70-76.

Cabrera et al., "Usefulness of an alcohol soluction of N-duopropenide for the surgical antisepsis of the hands compared with handwashing with iodine-povidone and chlrohexidine: clinical essay," Journal of Surgical Research 94 (2000) pp. 6-12.

Cafferkey et al., "Post-operative urinary infection in urology," Letters to the Editor, Journal of Hospital Infection pp. 391-392.

DeRiso et al., "Chlorhexidine Gluconate 0.12% Oral Rinse Reduces the Incidence of Total Nosocomial Respiratory Infection and Nonprophylactic Systemic Antibiotic Use in Patients Undergoing Heart Surgery," American College of Chest Physicians (Jun. 1996) pp. 1556-1561.

Dzubow et al., "Comparison of preoperative skin preparations for the face," Journal of American Academy of Dermatology, vol. 19, No. 4 (Oct. 1988) pp. 737-741.

Eldridge et al., "Efficacy of an alcohol-free chlorhexidine mouthrinse as an antimicrobial agent," The Journal of Prosthetic Dentistry, vol. 80 No. 6 (Dec. 1998) pp. 685-690.

Freeman, "Sterilization and antiseptics," Surgical Methods, Chapter 10 (2006) pp. 112.

Gevaudan et al., "Study of the efficacy of an alcoholic solution of chlorhexidine at 0.5% for hand antisepsis," Medicine and Infectious Diseases vol. 14 No. 3, (1984) pp. 94-101.

Hayek et al., "A placebo-controlled trial of the effect of two preoperative baths or showers with chlrohexidine detergent on postoperative wound infection rates," Journal of Hospital Infection (1987) pp. 165-172.

Houston et al., "Effectiveness of 0.12% Chlorhexidine gluconate oral rinse in reducing prevalence of noscocomial pneumonia in patients undergoing heart surgery," American Journal of Critical Care, vol. 11, No. 6 (2002) pp. 567-570.

Junor et al., "Sclerosing peritonitis—the contribution of chlorhexidine in alcohol," Peritoneal Dialysis International (Sep. 20, 2010) pp. 1-5.

Kramer et al., "Alcohol/chlorhexidine hand hygiene products," VQC Hand Hygiene Product—Literature Review (2002) pp. 1-12.

Larson et al., "APIC guideline for handwashing and hand antisepsis in health care settings," APIC Guidelines for Infection Control Practice (Aug. 1995) pp. 251-269.

Legras et al., "Prospective randomized study for prevention of infections associated with alcoholic chlorhexidine catheters against polyvidone iodine," Rean Urg (1997) pp. 5-11.

Lowbury et al., "Use of 4% Chlorhexidine detergent solution (Hibiscrub) and other methods of skin disinfection," British Medical Journal (1973) pp. 510-515.

Maki et al., "Prospective randomized trial of povidone-iodine, alcohol, and chlorhexidine for prevention of infection associated with central venous and arterial catheters," AJIC American Journal of Infection Control (1994) pp. 242.

Maki et al., "Prospective randomized trial of povidone-iodine, alcohol, and chlorhexidine for prevention of infection associated with central venous and arterial catheters," AJIC American Journal of Infection Control, vol. 338 (Aug. 10, 1991) pp. 339-343.

Millns et al., "The sensitivity to chlorhexidine and ceyyl pyridinium chloride of staphylococci on the nands of dental students and theatr staff exposed to these disinfectants," Journal of Hospital Infection (1994) pp. 99-104.

Mitchell, "Whole body disinfection with chlorhexidine: is shower bathing more effecting than bathing?," Journal of Hospital Infection (1984) pp. 96-99.

Montefiori et al., "Effective inactivation of human immunodeficiency virus with chlorhexidine antiseptics containing detergents and alcohol," Journal of Hospital Infection (1990) pp. 279-282.

(56) References Cited

OTHER PUBLICATIONS

Regent Medical Ltd., "Safety Data Sheet," Hibiscrub Red (Nov. 28, 2005) pp. 1-4.
Rotter et al., "A comparison of the effects of preoperative whole-body bathing with detergent alone and with detergent containing chlorhexidine gluconate on the frequency of wound infections after clean surgery," Journal of Hospital Infection (1988) pp. 310-320.
The Department of Health and NHS Purchasing and Supply Agency, The Results Using Technology to Help Fight Infection, "ChloraPrep[ 2% Chlorhexidine Gluconate w/v 70% Isopropyl Alcohol v/v cutaneous solution for skin antisepsis" (Aug. 26, 2009) pp. 1-31.
Trautner et al., "Skin antispsis kits containing alcohol and chlorhexidine gluconate or tincture of iodine are associated with low rates of blood culture contamination," Infection Control and Hospital Epidemiology, vol. 23, No. 7 (Jul. 2002) pp. 397-401.
Wai-Kei et al., "Sclerosing peritonitis complicating prolonged use of chlorhexidine in alcohol in the connection procedure for continuous ambulatory peritoneal dialysis," Peritoneal Dialysis International, vol. 11, (1991) pp. 166-172.
Weber et al., "Efficacy of selected hand hygiene agents used to remove bacillus atrophaeus (a surrogate of bacillus anthracis) from contaminated hands," JAMA, vol. 289, No. 10 (Mar. 12, 2003).
Weinstock et al., "A Novel Staff Vaccination," Letters to the Editor, vol. 23 No. 5, Infection Control and Hospital Epidemiology (May 2002), pp. 232-235.
Zamany et al., "The effect of chlorhexidine as an endodontic disinfectant," Oral Surgery Oral Medical Oral Pathology, vol. 96, No. 5 (Nov. 2003) pp. 578-581.
Extended European Search Report for Application No. 18865613.6 dated Nov. 12, 2021.

\* cited by examiner

ANTISEPTIC WIPES

FIELD

The disclosure is in the field of patient care products and in various non-exclusive embodiments is specifically directed to antiseptic wipes that can be used to disinfect the skin of a patient prior to or after a surgical operation.

BACKGROUND

It is desirable for a surgical site on a patient's skin to be substantially free of dirt and active pathogens prior to surgery. Medical workers can clean the skin of a patient or the patient can perform the cleaning. Known pre-operative cleaning processes include showering, bathing, rinsing, and wiping. It is also desirable to maintain the cleanliness of a surgical site post-operation. Surgical sites are commonly cleaned using aqueous or alcohol-based antiseptic solutions, including for example solutions that contain chlorhexidine gluconate.

It has now been found that a cleansing wipe containing a cleansing composition formulated with chlorhexidine gluconate can be made to meet the responder rates required by the Tentative Final Monograph (TFM) for OTC Healthcare Antiseptic Drug Products—Jun. 17, 1994 (TFM-1994) for eight hours. The composition may be formulated to include a wetting agent and defoamer, and other ingredients added to provide certain advantageous properties. The wipe preferably is composed of a nonwoven plurality of fibers, such as polyester fibers, having a denier ranging from 2.6 to 3.7.

Relatedly, a method of disinfecting skin can comprise applying the wipe to skin. A wipe can be included in a package that is sealed so as to preserve the sterile nature of the wipe before the package is opened. In some embodiments, a method of disinfecting skin comprises opening a package, removing a wipe, and applying the wipe to skin. A wipe can also be used in a method of preparing skin for surgery, including applying the wipe to skin, up to eight hours before the surgical procedure.

Also provided is a method of making a wipe including preparing a cleansing composition and disposing the cleansing composition on a cloth. A method of packaging wipes can comprise placing at least two wipes in a package and then sealing the package.

DETAILED DESCRIPTION

Figure 1:
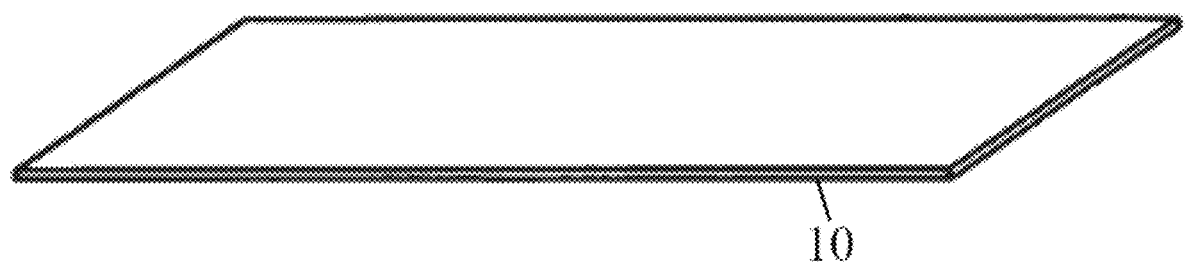
FIG. 1 is a perspective illustration of a plurality of wipes made in accordance with the present disclosure.

Generally, a wipe includes a cleansing composition disposed on a cloth. The cleaning composition is generally aqueous and includes purified, sterile water as a solvent or vehicle. The cleansing composition further comprises an antiseptic, a humectant, an emollient, a wetting agent, a monohydric alcohol as a defoamer, and water.

Any suitable antiseptic can be included in a cleansing composition. An exemplary antiseptic includes one or more of a biguanide, octenidine dihydrochloride, a quaternary ammonium compound, an alcohol, an iodine preparation, a peroxide, polyhexanide, a quinolone compound, an antimicrobial dye, a permanganate, a halogenated phenol compound, etc. Exemplary biguanides include chlorhexidine gluconate, chlorhexidine acetate, alexidine, derivatives and mixtures thereof. The antiseptic is included in an amount ranging from 0.01 to 10%, 0.1 to 5%, or 1 to 3% by weight of the cleansing composition.

Any suitable humectant can be included in a cleansing composition to aid in increasing moisture content of skin. Exemplary humectants include any one or more of collagen, a polyhydric alcohol, urea, etc. Useful polyhydric alcohols include butylene glycol, glycerin, hexylene glycol, polyalkylene glycols such as polyethylene glycol and polypropylene glycol, propylene glycol, dipropylene glycol, sorbitol, Methylene glycol, arylpropyne glycol, alkaline polyols 1,3-dibutylene glycol, allantoin, derivatives and mixtures thereof, etc. In some embodiments, a humectant is included in an amount ranging from 0.3 to 15%, 1 to 10%, or 3 to 8% by weight of the cleansing composition. Exemplary cleansing compositions include at least one selected from glycerin and propylene glycol. An embodiment of a cleansing composition comprises both glycerin and propylene glycol.

A cleansing composition can include any suitable emollient to condition or otherwise soften skin. Exemplary emollients include any one or more of a fatty acid such as caprylic acid, lauric acid, myristic acid, oleic acid, palmitic acid, and stearic acid; a fatty ester such as glyceryl stearate, isopropyl myristate, and isopropyl palmitate; a fatty alcohol such as cetearyl alcohol, cetyl alcohol, lauryl alcohol, oleyl alcohol, and stearyl alcohol; a silicone such as cyclomethicone, cyclopentasiloxane, polydimethylsiloxane (dimethicone), dimethiconol, dimethicone crosspolymer, phenyl trimethicone, trisiloxane; petrolatum; derivatives thereof, etc. In some embodiments, an emollient is included in an amount ranging from 0.05 to 1%, 0.1 to 0.8%, or 0.2 to 0.4% by weight of the cleansing composition. In an exemplary embodiment, a cleansing composition includes dimethicone 350. Dimethicone 350 is available as DOW CORNING® Q7-9120 Silicone Fluid, 350 cst. Another suitable dimethicone is DOW CORNING® Dimethicone 365.

Any suitable wetting agent or surfactant can be included in a cleansing composition. Exemplary surfactants include any one or more of cationic surfactants such as benzalkonium chloride and cetrimonium chloride; anionic surfactants such as sodium lauryl sulfate, disodium laureth sulfosuccinate, sodium lauroyl sarcosinate, sodium cocoyl isethionate, and sodium methyl cocoyl taurate; amphoteric surfactants such as sodium lauriminodipropionate, disodium cocoamphodipropionate, and disodium lauroamphodiacetate; and non-ionic surfactants such as polysorbate 20, octoxynol-9, glyceryl oleate, and sorbitan oleate. In some embodiments, a surfactant is included in an amount ranging from 0.004 to 0.5%, 0.02 to 0.3%, or 0.05 to 0.15% by weight of the cleansing composition. Exemplary cleansing compositions comprise benzalkonium chloride as a wetting agent and a secondary surfactant comprising at least one of octoxynol-9, and polysorbate 20. In an exemplary embodiment, the cleansing composition includes each of benzalkonium chloride, oxtoxynol-9, and polysorbate 20.

In some aspects, a cleansing composition comprises or consists essentially of chlorhexidine gluconate in an amount ranging from 1 to 3%, glycerin in an amount ranging from 2 to 8%, propylene glycol in an amount ranging from 0.5 to 3%, isopropyl alcohol in an amount ranging from 0.2 to 0.8%, dimethicone in an amount ranging from 0.1% to 0.4%, benzalkonium chloride in an amount ranging from 0.02 to 0.08%, octoxynol-9 in an amount ranging from 0.005 to 0.1%, polysorbate 20 in an amount ranging from 0.005 to 0.1%, and the balance of water, all percentages being by weight of the cleansing composition.

An aqueous cleansing composition may optionally include an emulsifier in an amount effective to impart affinity of the cleansing composition to a hydrophobic cloth. Any suitable emulsifying agent may be used. Preferable emulsifying agents include fatty alcohols, such as $C_{14-22}$ alcohols, or alkyl aldosides, and in particular alkyl glucosides and even more particularly, $C_{12-20}$ alkyl glucosides. A particularly preferred emulsifying agent is cetyl alcohol. Other emulsifying agents include MONTANOV L and MONTANOV S, each available from Seppic. MONTANOV L is a proprietary mixture of $C_{14-22}$ alcohols and $C_{12-20}$ alkyl glucoside for the preparation of a O/W (oil-in-water) emulsion. MONTANOV S is a mixture of coco glucoside and coconut alcohol. The emulsifier can be present in any amount suitable for the purpose stated above. In some embodiments, the emulsifier can be present in an amount ranging from 1-2% by weight of the cleansing composition. In some cases the emulsifier comprises at least emulsifying agents selected from among the $C_{14-22}$ alcohols, $C_{12-20}$ alkyl glucosides, coco glucosides, coconut alcohols, and mixtures thereof.

FIG. 1 depicts a plurality of wipes 10. The cloth of the wipes can be hydrophobic or hydrophilic and constructed of natural or synthetic fiber, such as cotton, wool, silk, polyester, rayon, nylon, polyethene, polypropylene, polyolefin, polyamide, etc. In exemplary embodiments, the cloth is made of fiber of a single composition, such as only polyester fiber. In some embodiments, the denier of the fiber in the cloth is substantially uniform such that the cloth has a denier variance ranging from 0.05 to 0.09, 0.06 to 0.08, or 0.074 to 0.078. In some embodiments, the denier of the fiber in the cloth ranges from 2.0 to 4.0, from 2.6 to 3.7, or from 2.8 to 3.6. A cloth can be made of fiber of any length. Embodiments of the cloth include fiber having substantially uniform length ranging from 65 to 85 mm, 70 to 80 mm, or 74 to 76 mm. The cloth can be woven and made by weaving, or more preferably non-woven and formed by non-woven methods. A cloth can be flat or tufted. In some embodiments, the cloth can be formed in a sheet or mat. An exemplary nonwoven cloth is made of polyester fiber with denier ranging from 2.6 to 3.7 and fiber length from 74 to 76 mm.

The cleansing composition may further include other ingredients such as fragrances, colors, preservatives, and additives to modify the pH. These ingredients may be added in any amounts suitable for their intended purposes.

Any suitable fragrance may be included in a cleansing composition. Exemplary fragrances include one or more selected from vanilla crème extract and chamomile extract.

One suitable preservative is EUXYL® PE9010, available from Schülke & Mayr GmbH. This is a liquid cosmetic preservative that is based on phenoxyethanol and ethylhexyl glycerin. The preservative may be present in any amount effective to provide a property of preservation. For example, the preservative may be present in an amount of about 0.1%-1.5% by weight of the cleansing composition.

The pH of a cleansing composition can, if desired, be adjusted to a range compatible with the (average) pH of healthy skin, to a range so as to compensate for the pH of residues that otherwise may remain on the skin after cleansing with a wipe, or to a range more inhospitable to pathogens. For instance, adjusting the pH to not more than 5.5 or 6 is consistent with the pH of healthy skin being approximately 5. Compensating for residues that may otherwise be alkaline can be achieved by adjusting the pH to a range less than 5, perhaps as low as 4, even down to a pH of 3 in some cases. However, too low a pH can lead to skin irritation. The pH can range from about pH 3 to about pH 9, particularly from about pH 4 to about pH 7.5. Compounds for adjusting the pH can be suitably selected from dermatologically acceptable pH control agents, agents suitable for skin care products and the like. Compounds include, for example, fruit acids such as citric acid, conjugate bases like citrates such as sodium citrate or trisodium citrate, gluconic acid, lactic acid, glycolic acid, lactates such as sodium lactates, malic acid, malates such as sodium malate, as well as mixtures of any thereof. The compound(s) to be selected should be compatible with other ingredients in a cleansing composition.

The cleansing composition further may include any suitable thickener. In general, thickeners include certain ingredients that can also serve as thickeners (viscosity-increasing agents). Typically, such viscosity increasing agents include, but are not limited to, hydrogenated vegetable oils like hydrogenated jojoba oil and hydrogenated jojoba wax; microcrystalline wax; paraffin wax; beeswax; carnauba wax; ozokerite wax; ceresine wax; myristyl alcohol; behenyl alcohol; stearyl alcohol; cetearyl alcohol; hydrogels; and mixtures thereof. It will be appreciated that other modifiers that can function as thickeners may be suitably selected.

A cleansing composition can include other ingredients as suitable for their intended purposes. Other adjunctive ingredients can include texturizers, anti-oxidants, pH buffers, metal sequestrants, and anti-stick agents.

Also encompassed in various alternative embodiments are a method of making a wipe, and a method of packaging wipes, a package comprising at least two wipes, a method for disinfecting skin, and a method of preparing skin for surgery.

Figure 2:
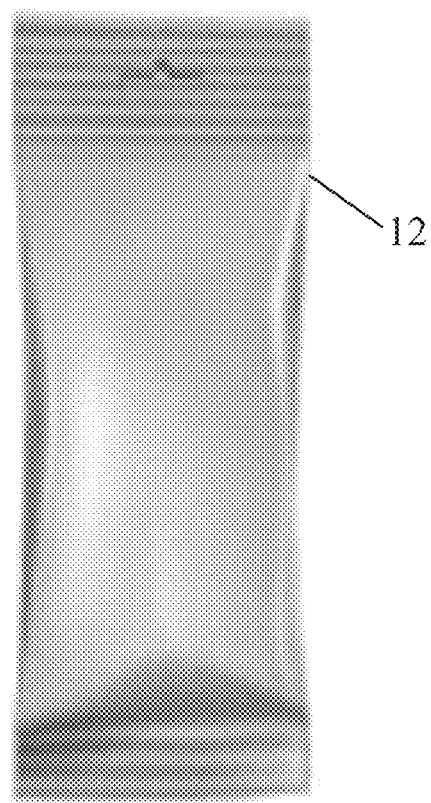
FIG. 2 is a perspective illustration of a package of wipes made in accordance with the present disclosure.

To make a wipe, generally, a cleansing composition as described hereinabove is first prepared and then disposed on the cloth. The temperature when mixing components of the cleansing composition can be any suitable temperature. The cleansing composition can be disposed on the cloth using any suitable means, such as by immersion in a bath or by spraying. A cloth as described hereinabove may be provided as a roll of material that may be cut to the desired dimensions of a wipe. A cleansing composition may be disposed on a cloth before or after cutting the cloth to the desired shape. After disposing the cleansing composition on the cloth, the prepared wipes can be stacked in a folded or non-folded orientation. The wipes may be placed in a package (such as package 12, illustrated in FIG. 2) using conventional packaging equipment. Any suitable number of wipes, such as two wipes, may be placed within a package. The package can then be sealed to preserve the integrity of the wipes. A package can include any number of wipes, and preferably includes at least two wipes. A package preferably has a conventionally sealed closure and the contents of the package are preferably sterile prior to opening the package.

A method of disinfecting skin can include applying a wipe as described herein to skin. The wipe can be applied to the skin of a patient by a caretaker, a medical worker, or by the patient. When disinfecting skin, a package can be opened by any means such as tearing, cutting, rupturing, etc. the package, or opening a permanently sealed or resealable closure. After opening the package, a wipe can be removed and applied to skin.

When a wipe is applied to the skin, the cleansing composition emanates from the cloth and onto the skin. The wipe described herein can be used as a pre-operative or a post-operative wipe for disinfecting skin at a surgical site. For sanitary purposes, the wipe can also be used for disinfecting skin that has not or will not undergo surgery. While wipes described herein can be applied to skin as frequently as desired, it is preferable that the wipes not be applied to a surgical site more than about eight hours prior surgery. The wipe may be applied to cleanse the skin at any suitable time before surgery, such as within one hour prior to surgery, within two hours prior to surgery, within three hours prior to surgery, within four hours prior to surgery, within five hours prior to surgery, within six hours prior to surgery, within seven hours prior to surgery, within eight hours prior to surgery, or at eight hours prior to surgery.

The following example is provided to illustrate the present invention but should not be construed as limiting a scope of the invention.

Example

A cleansing composition was made by combining 2% chlorhexidine gluconate (specific gravity 1.02, density 1.017 g/mL), 5% glycerin, 1.5% propylene glycol, 0.5% isopropyl alcohol, 0.75% Dimethicone 365 emulsion, benzalkonium chloride, and the balance purified water, all percentages by weight of the cleansing composition.

The obtained cleansing composition was disposed on nonwoven polyester cloth having a maximum denier of 3.59, a minimum denier of 2.88, an average denier of 3.22, and a denier variance of 0.076, to obtain a plurality of wipes.

Two separate studies, including respectively 340 and 347 volunteer subjects, were conducted on the example wipe under randomized conditions to measure antimicrobial efficacy as specified under Tentative Final Monograph (TFM) for OTC Healthcare Antiseptic Drug Products—Jun. 17, 1994 (TFM-1994). In both studies, the exemplary wipe was topically applied to skin by vigorously scrubbing skin in a back and forth motion for up to three minutes per treatment area (abdomen or groin). In both studies, the exemplary wipe met the required responder rates as defined under TFM-1994 for up to 8 hours.

All percentages stated herein are weight percentages.

Uses of singular terms such as "a," "an," are intended to cover both the singular and the plural, unless otherwise indicated herein or clearly contradicted by context. The terms "comprising," "having," "including," and "containing" are to be construed as open-ended terms. Any description of certain embodiments as "preferred" embodiments, and other recitation of embodiments, features, or ranges as being preferred, or suggestion that such are preferred, is not deemed to be limiting. The invention is deemed to encompass embodiments that are presently deemed to be less preferred and that may be described herein as such. All methods described herein can be performed in any suitable order unless otherwise indicated herein or otherwise clearly contradicted by context. The use of any and all examples, or exemplary language (e.g., "such as") provided herein, is intended to illuminate the invention and does not pose a limitation on the scope of the invention. Any statement herein as to the nature or benefits of the invention or of the preferred embodiments is not intended to be limiting. This invention includes all modifications and equivalents of the subject matter recited herein as permitted by applicable law. Moreover, any combination of the above-described elements in all possible variations thereof is encompassed by the invention unless otherwise indicated herein or otherwise clearly contradicted by context. The description herein of any reference or patent, even if identified as "prior," is not intended to constitute a concession that such reference or patent is available as prior art against the present invention. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A wipe comprising:
    a nonwoven cloth comprising plural fibers having a denier in the range from 2.6 to 3.7, the nonwoven cloth having a denier variance ranging from 0.05 to 0.09, and
    a cleansing composition disposed on the cloth, the cleansing composition comprising chlorhexidine gluconate in an amount sufficient to reduce the number of active pathogens present on skin upon contact between the cleansing composition and the skin, a monohydric alcohol in an amount effective to provide a defoaming effect, a wetting agent, and water.

2. A wipe according to claim 1, the cleansing composition comprising chlorhexidine gluconate, isopropyl alcohol, and benzalkonium chloride.

3. A wipe according to claim 1, further comprising dimethicone.

4. A wipe according to claim 1, further comprising a humectant.

5. A wipe according to claim 1, further comprising an additional surfactant.

6. A wipe according to claim 5, the additional surfactant comprising at least one of octoxynol-9 and polysorbate 20.

7. A wipe according to claim 1, the cleansing composition consisting essentially of chlorhexidine gluconate, glycerin, propylene glycol, isopropyl alcohol, dimethicone, and benzalkonium chloride.

8. A wipe according to claim 7, the cleansing composition consisting essentially of chlorhexidine gluconate in an amount ranging from 1 to 3%, glycerin in an amount ranging from 2 to 8%, propylene glycol in an amount ranging from 0.5 to 3%, isopropyl alcohol in an amount ranging from 0.2 to 0.8%, dimethicone in an amount ranging from 0.1% to 0.4%, benzalkonium chloride in an amount ranging from 0.02 to 0.08%, and water.

9. A method of disinfecting skin comprising applying the wipe according to claim 1 to skin.

10. A method according to claim 9, the method comprising applying the wipe according to claim 1 within eight hours prior to a surgical procedure.

11. A package comprising a container having contained therewithin at least two wipes according to claim 1.

12. A method of making a wipe, the method comprising:
    preparing a cleansing composition consisting essentially of chlorhexidine gluconate in an amount ranging from 1 to 3%, glycerin in an amount ranging from 2 to 8%, propylene glycol in an amount ranging from 0.5 to 3%, isopropyl alcohol in an amount ranging from 0.2 to 0.8%, dimethicone in an amount ranging from 0.1% to 0.4%, benzalkonium chloride in an amount ranging from 0.02 to 0.08%, and water; and
    introducing the cleansing composition onto a nonwoven cloth having a denier ranging from 2.6 to 3.7 and a denier variance ranging from 0.05 to 0.09.

13. A wipe according to claim 1, further comprising octoxynol-9.

14. A wipe according to claim 1, further comprising an anionic surfactant.

15. A wipe according to claim 14, the anionic surfactant comprising at least one of sodium lauryl sulfate, disodium laureth sulfosuccinate, sodium lauroyl sarcosinate, sodium cocoyl isethionate, and sodium methyl cocoyl taurate.

16. A wipe comprising:
   a nonwoven cloth comprising substantially uniform plural fibers all having a denier in the range from 2.6 to 3.7, and
   a cleansing composition disposed on the cloth, the cleansing composition comprising chlorhexidine gluconate in an amount sufficient to reduce the number of active pathogens present on skin upon contact between the cleansing composition and the skin, a monohydric alcohol in an amount effective to provide a defoaming effect, a wetting agent, and water.

17. A wipe according to claim 16, the cleansing composition comprising chlorhexidine gluconate, isopropyl alcohol, and benzalkonium chloride.

18. A wipe according to claim 17, the cleansing composition consisting essentially of chlorhexidine gluconate, glycerin, propylene glycol, isopropyl alcohol, dimethicone, and benzalkonium chloride.

19. A wipe according to claim 18, the cleansing composition consisting essentially of chlorhexidine gluconate in an amount ranging from 1 to 3%, glycerin in an amount ranging from 2 to 8%, propylene glycol in an amount ranging from 0.5 to 3%, isopropyl alcohol in an amount ranging from 0.2 to 0.8%, dimethicone in an amount ranging from 0.1% to 0.4%, benzalkonium chloride in an amount ranging from 0.02 to 0.08%, and water.

20. A wipe according to claim 19, further comprising an anionic surfactant, the anionic surfactant comprising at least one of sodium lauryl sulfate, disodium laureth sulfosuccinate, sodium lauroyl sarcosinate, sodium cocoyl isethionate, and sodium methyl cocoyl taurate.

* * * * *